United States Patent
Mohanlal

(10) Patent No.: US 7,198,895 B2
(45) Date of Patent: Apr. 3, 2007

(54) IN VITRO CELL-BASED METHODS FOR BIOLOGICAL VALIDATION AND PHARMACOLOGICAL SCREENING OF CHEMICAL ENTITIES AND BIOLOGICALS

(76) Inventor: Ramon W. Mohanlal, 35 Park Dr., Apt. 18, Boston, MA (US) 02215

( * ) Notice: Subject to any disclaimer, the term of this patent is extended or adjusted under 35 U.S.C. 154(b) by 3 days.

(21) Appl. No.: 10/008,107

(22) Filed: Nov. 13, 2001

(65) Prior Publication Data

US 2003/0054362 A1    Mar. 20, 2003

Related U.S. Application Data

(60) Provisional application No. 60/248,410, filed on Nov. 14, 2000.

(51) Int. Cl.
*C12Q 1/68* (2006.01)

(52) U.S. Cl. .............................. 435/6; 514/1
(58) Field of Classification Search .................... 435/6; 514/1

See application file for complete search history.

(56) References Cited

U.S. PATENT DOCUMENTS

| | | | |
|---|---|---|---|
| 6,242,202 B1 * | 6/2001 | H.ang.kansson | ........... 435/7.23 |
| 6,801,859 B1 * | 10/2004 | Friend et al. | ................. 702/19 |
| 2003/0113831 A1 * | 6/2003 | Hakonarson | ................. 435/29 |
| 2003/0134776 A1 * | 7/2003 | Hakonarson | .................... 514/1 |

FOREIGN PATENT DOCUMENTS

WO    WO 96/35948    11/1996

OTHER PUBLICATIONS

Villeneuve et al., Current Topics in Medicinal Chemistry 4(13), 1453 (2004 Abstract).*
Hess et al., 2001, Trends Biotechnol. 19(11): 463-468.
Liggett, 2001, Nature Medicine 7:281-283.
Busse et al., 2001, NEJM 344: 350-362.
Wilber et al., 2000, Annals of Emergency Medicine 36: 427-431.
Drysdale et al., 2000, PNAS 97:10483-10488.
Burczynski et al., 2000, Toxicological Sciences 58: 399-415.
Nielsen et al., 2000, J. Immunology 165 (4): 2287-2296.
Kang et al., 2000, J. Biol. Chem. 275:8742-8748.
Drews, 2000, Science 287: 1960-1964.
Nanki et al., 2000, J. Immunology 164 (10): 5010-5014.
Beerli et al., 2000, PNAS 97: 1495-1500.
Naldini et al., 2000, Advances in Viral Research 55: 599-609.
Ohlstein et al., 2000, Annu. Rev. Pharmacol. Toxicol. 40: 177-191.
Poste, 2000, Scrip Magazine 11-14.
Afshari et al., 1999, Cancer Research 59: 4759-4760.
Drazen et al., 1999, Nature Genetics 22: 168-170.
Aurran-Schleinitz et al., 1999, Br. J. Haematol. 106: 357-367.
Pollard et al., 1999, Br. J. Haematol. 106: 538-544.
Nuwaysir et al.; 1999, Mol. Carcinog. 24:153-159.
Galbraith, 1999, Methods in Cellular Biology 58: 315-341.
Beerli et al., 1998, PNAS 95: 14628-14633.
Bejarano et al., 1998, Blood 92: 4256-4562.
Kim et al., 1998, PNAS 95: 2812-2817.
Luxembourg et al., 1998, Nature Biotechnology 16: 281-285.
Braxton et al., 1998, Curr. Opin. Biotech. 9:643-649.
Berki et al, 1998, J. Immunological Methods 214 (1-2): 19-27.
Martinez et al., 1997, J. Clin. Invest. 100: 3184-3188.
Blaiss, 1997, JAMA 278: 1874-1879.
Riese et al., 1995, Molecular and Cellular Biology 15: 5770-5776.
Barnes, 1995, NEJM 332: 868-875.
Green et al., 1995, Am. J. Respir. Cell Mol. Biol. 13:25-33.
Hirano et al., 1994, Transplantation 57:1341-1348.
Reichert et al., 1991, Clin. Immunol. Immunopathol. 60: 190-208.
Pierce et al., 1988, Science 239: 628-631.
Motojima et al., 1983, Allergy 38:331-337.
Jenne, 1982, J. Allergy Clin. Immunol. 70:413-416.
Gillespie et al., 1974, J. Allergy Clin. Immunol. 53: 27-33.
Parker et al., 1973, J. Clin. Invest. 52: 48-59.
Boyum, 1964 Nature 204:793-794.

* cited by examiner

*Primary Examiner*—Kenneth R. Horlick
(74) *Attorney, Agent, or Firm*—Cheryl H. Agris

(57) ABSTRACT

This patent describes a novel in vitro cell-based method for biological validation and pharmacological screening of drugs, new chemical entities (NCEs) and biologics, which is predictive of in vivo testing for efficacy and adverse events in patients, as occurs in clinical trials. The same method can be used to create an in vitro cell-based assay to identify the 'right marketed medication for the right patient' (personalized medicine), and to identify responders/non-responders in ongoing clinical trials with NCEs. In addition this approach can be used to identify new indications for existing medicines and new indications for NCEs that were unsuccessful in their intended uses.

10 Claims, No Drawings

IN VITRO CELL-BASED METHODS FOR BIOLOGICAL VALIDATION AND PHARMACOLOGICAL SCREENING OF CHEMICAL ENTITIES AND BIOLOGICALS

RELATED APPLICATIONS

This application claims priority from U.S. Ser. No. 60/248,410 filed on Nov. 14, 2000, which is incorporated by reference in its entirety.

BACKGROUND OF THE INVENTION

The pharmaceutical industry spends more than $40 billion worldwide on research and development of new drugs, but only 5 to 10% of drugs entering the clinical phase of drug development will be approved for marketing. Currently the average cost per successful drug development program is between $500 and $900 million, and its duration is on average 8 to 12 years (1,2,3). This average cost figure is this high because 75% of that $500–900 million the pharmaceutical companies spend per drug is related to drug failures along the way (2).

An important reason for the high failure rate in clinical trials is the poor predictive value of currently used screening technologies for biological validation, pharmacological testing, and screening for success or failure of chemical entities and biologicals in clinical trials involving human subjects. These screening technologies are based on in vitro cell-based screening models and in vivo animal models, which often lack or inadequately represent the clinical disease phenotype of the patients in which the tested chemical entities or biologicals are intended to be used in the future. Therefore, success of these chemical entities or biologicals in these models does not necessarily translate into clinical success in patients. Hence, the majority of chemical entities or biologicals, while successful in these preceding screening and animal models, fail in clinical trials, particularly in late phase II and phase III trials (38). It has been estimated that more than 90% of new chemical entities (NCEs) fail in clinical trials, of which approximately two third fail for pharmacodynamic reasons (lack of efficacy and/or an unacceptable adverse event profile); the remaining third fail for pharmacokinetic reasons (3).

According to a Lehman Brothers report, the problem of poorly predictive models will become increasingly worse in the genomic era because a higher number of inadequately biologically validated NCEs will enter clinical trials (1). This will decrease the overall success rate of clinical trials even further. This report predicts that the average R&D budget needed to develop an NCE will have to increase from a current value of $500–900 million to $1.5 billion in the next five years, unless significant improvements are made.

The lack of available predictive technologies for success or failure in clinical trials leads to the current situation. Long and expensive preceding studies (in general more than five years and upfront investments of tens to hundreds of million dollars) are needed both in animals and humans before success or failure of NCEs can be established in phase II or phase III studies. Until better models are developed, the majority of NCEs will fail in phase II and III trials, either due to lack of efficacy or an unfavorable side effect profile. A cell-based method that could better predict success or failure in phase II and III trials, without the need for large up front investments, would represent a tremendous advantage from a pharmaco-economic perspective, as it would eliminate drug candidates or biologicals likely to fail early on, without the requirement of large upfront investments. Eventually, such a method would allow the production of medicines that are safer and more effective, at a much-reduced cost. In addition, such a model would reduce the need for in vivo animal testing.

Furthermore, most drugs show significant inter-individual variation in therapeutic efficacy and adverse event outcome (4,5,6,7,8). Evaluation of effectiveness and adverse event profile is still based on the average response of a study group. Inspection of the data from individual subjects, however, usually reveals significant numbers of patients with little or no response, as well as those who have dramatic responses. In cases of complex diseases, this 'one-drug-fits-all' attitude subjects patients to empirical trial-and-error periods before acceptable treatment regiments are found (4,8).

Assays for the personalized medicine application and the identification of responders/non-responders in clinical trials are currently based on single nucleotide polymorphisms (SNPs) or haplotypes (4,8). Despite major investments made to develop the SNP approach for these applications, the numbers of successfully developed assays are small and their predictive value is often only modest. The trial-and-error nature of current clinical practice is a significant economic burden on the health care system and keeps many patients effectively untreated for sustained periods of time. A test tool that could predict whether a registered medication would be effective in a specific patient in a timely manner would offer tremendous benefit for patients and healthcare economics.

Moreover, the same principle could also be used to identify responders/non-responders in clinical trials with not yet registered NCEs. A large number of patients has to be recruited for each individual clinical phase II and III trials, in order to demonstrate efficacy and safety in a statistically meaningful manner. Typically 50 to 200 patients are recruited in phase II and hundreds to thousands of patients in phase III. An important reason for the large numbers of patients are needed is the strong inter-individual variation in therapeutic efficacy and adverse event outcome in a randomly recruited patient population. The elimination of non-responders in these clinical trials would reduce the variability in trial outcome. This, in turn, would reduce the need for a large sample size of patients dramatically. Therefore, a test tool that avoids inclusion of patients likely to be non-responders in a clinical trial would lead to cost reduction on the order of hundreds of millions up to billions of dollars.

The development of predictive cell-based models has been hampered for various reasons, including the availability of human cells and tissues, in particular with the right genotype and disease phenotype, and the identification of validated cellular endpoints that have proven to predict in vivo responses after drug exposure. An ideal cell-based model should be using target cells or target tissues from patients who would be ultimately treated with the tested dugs. The availability of human cells for drug testing is limited, and often from questionable quality due to limitations in the preservation and the homogeneity of excised human tissues. Embryonic stem cell-based technologies are currently considered, but have inherent restrictions due to ethical considerations, and limitations in defining disease phenotype in these embryos that do not have manifestations of disease to be treated by investigational drugs or biologicals. Therefore the value of embryonic stem cells to predict pharmaco-responses in specific patient populations with a well-defined disease phenotype is restricted. The identification of cellular pharmaco-response that reliably predicts pharmaco-responses in real patients with defined disease phenotype is another important obstacle. Ideally, this would require an experimental setting in which both cellular endpoints and in vivo patient endpoints after exposure to the same drug can be obtained to allow for a within-subject comparison, and to establish a strong in vitro/in vivo correlation.

Accordingly, a need remains in the art for a cell-based assay that can better predict success or failure of NCEs in phase II and III trials. A need also remains in the art for an assay that can identify patients likely to be non-responders in a clinical trial. Finally, a need remains in the art for an assay that can predict whether a medication or a chemical entity will be effective in a specific patient.

SUMMARY OF THE INVENTION

The present invention provides an in vitro method of predicting an in vivo response in a patient to a chemical entity. Such a method generally comprises creating a reference set of cellular responses in peripheral blood mononuclear cells ("PBMCs"), which are extracted from groups of subjects, each group exposed to a different chemical entity, approved for treatment of a certain disease indication. These cellular responses are classified by the clinical indication of the subjects from whom the PBMCs are extracted. The reference set can also include in vivo responses for efficacy and/or safety (adverse events profile) of the same subjects to the group of chemical entities to which the cellular responses are correlated, in order to create cellular response profiles. The method further comprises drawing PBMCs from a patient suffering from the same disease indication for whom the predicted in vivo response is desired, detecting the cellular response of the patient's PBMCs to a chemical entity, then finding the in vivo response to which the cellular response corresponds in the reference set by using the cellular response profiles. The patient, when exposed to the chemical entity in vivo, is predicted to have the in vivo response that corresponds with the cellular response in the reference set. The clinical indication may pertain to efficacy, adverse effect, or safety of the chemical entity. Examples of a chemical entity include a registered chemical entity, a novel chemical entity, an environmental reagent, or a biological. Examples of cellular response include gene expression, increased motility, chemotaxis, contraction, relaxation, biosynthesis, secretion of signaling molecules, depolarization, repolarization, degranulation, adhesion, aggregation, change in metabolic rate, or immediate cellular responses. Examples of PBMCs include T-lymphocytes, B-lymphocytes, monocytes, natural killer cells, or peripheral blood stem cells. The PBMCs obtained from the patient can be divided into two or more portions and each portion is tested on a different chemical entity.

In one embodiment, the detection of the cellular response of the patient's PBMCs to a chemical entity is accomplished by transducing the patient's peripheral blood mononuclear cells with a zinc finger protein that specifically expresses or upregulates the target for the chemical entity; exposing the transfected peripheral blood mononuclear cells to the chemical entity; performing mRNA extraction on the exposed peripheral blood mononuclear cells; constructing a cDNA library from the extracted RNA; performing a cDNA subtraction with another cDNA library; and detecting resultant cellular responses of the patient's peripheral blood mononuclear cells' to the chemical entity.

The present invention also provides a method of screening chemical entities for their efficacy in treating a disease. Such a method generally comprises drawing PBMCs from subjects diagnosed with a particular disease who have been treated with known chemical entities, then performing gene expression analyses on the subjects' PBMCs. These expression analyses results are then compared within the reference set and correlated to an in vivo response of the known chemical entities against the disease to create cellular response profiles. These cellular response profiles can then be used as markers for other chemical entities to predict their efficacy and/or adverse event profile in treating the disease. Again, the clinical indication may pertain to efficacy, adverse effect, or safety of the chemical entity. Examples of a chemical entity include a registered chemical entity, a novel chemical entity, an environmental reagent, or a biological. Examples of cellular response include gene expression, increased motility, chemotaxis, contraction, relaxation, biosynthesis, secretion of signaling molecules, depolarization, repolarization, degranulation, adhesion, aggregation, change in metabolic rate, or immediate cellular responses. Examples of PBMCs include T-lymphocytes, B-lymphocytes, monocytes, natural killer cells, or peripheral blood stem cells. The PBMCs obtained from the patient can be divided into two or more portions and each portion is tested on a different chemical entity.

In one embodiment, the gene expression analysis of the patient's PBMCs is obtained by drawing peripheral blood mononuclear cells from the patient diagnosed with the specific disease; performing gene expression analysis on the peripheral blood mononuclear cells of the patients; comparing the results of the gene expression analysis to a reference set of gene expression analysis results that are correlated with an in vivo response to the specific disease; and determining the in vivo response which correlates with the cellular response in the reference set.

The present invention further provides a method for detecting changes in gene expression in PBMCs in response to a chemical entity. Such a method generally comprises transfecting the PBMCs with zinc finger proteins ("ZFPs") that turn on genes encoding known targets for an effector, then exposing the PBMCs to the effector. The mRNA is then isolated from the PBMCs. Subtraction hybridization is used to eliminate all cDNAs expressed in unexposed PBMCs and/or expressed in clinical non-responders. The PBMCs are then assayed for the remaining over- and under-expressed cDNAs that indicate a difference in gene expression in response to the chemical entity. The detection of a remaining over- or under-expressed cDNA indicates a change in gene expression in the PBMCs in response to the chemical entity. Examples of a chemical entity include a registered chemical entity, a novel chemical entity, an environmental reagent, or a biological. Examples of PBMCs include T-lymphocytes, B-lymphocytes, monocytes, natural killer cells, or peripheral blood stem cells. The PBMCs obtained from the patient can be divided into two or more portions and each portion is tested on a different chemical entity.

Finally, the present invention provides a method for rapidly assessing whether a new patient diagnosed with a particular disease is likely to respond to a particular chemical entity. Such a method generally comprises creating a reference set of cellular responses to a group of chemical entities in PBMCs extracted from subjects who are classified by clinical indication and correlating them to in vivo responses from the same subjects in order to create cellular response profiles. These cellular response profiles are then captured on a suitable assay. PBMCs are drawn from the new patient and the cellular response to the chemical entity is detected. The new patient's cellular response is then compared to the cellular response profiles in the reference set to predict the chemical entity's in vivo response in the new patient. A patient having a cellular response that correlates with the cellular response in the reference set is likely to respond positively to the chemical entity. In one embodiment, the suitable assay is a microarray. In an alternative embodiment, the suitable assay is microbeads. The clinical indication may pertain to efficacy, adverse effect, or safety of the chemical entity. Examples of a chemical entity include a registered chemical entity, a novel chemical entity, an environmental reagent, or a biological. Examples of cellular response include gene expression, increased motility, chemotaxis, contraction, relaxation, biosynthesis, secretion of signaling molecules, depolarization, repolarization, degranulation, adhesion, aggregation, change in metabolic rate, or immediate cellular responses. Examples of PBMCs include T-lymphocytes, B-lymphocytes, monocytes, natural killer cells, or peripheral blood stem cells. The PBMCs obtained from the patient can be divided into two or more portions and each portion is tested on a different chemical entity.

In one embodiment, the detection of the cellular response of the patient's PBMCs is accomplished by transfecting the patient's PBMCs with a zinc finger protein that specifically expresses or upregulates the target for the chemical entity; exposing the transfected PBMCs to the chemical entity; performing mRNA extraction on the exposed PBMCs; constructing a cDNA library from the extracted RNA; performing a cDNA subtraction with another cDNA library; and detecting resultant cellular responses of the patient's PBMCs to the chemical entity.

DETAILED DESCRIPTION OF THE INVENTION

Definitions

In this invention, the following terms will be used as defined:

Zinc Finger Proteins (ZFP): Proteins that act as modulators of transcription for specific sequences of nucleic acids. One zinc finger domain makes base-specific contact with three base pairs. In one embodiment of the invention, a polydactyl protein of a 6-zinc finger domain equivalent, which makes contact with a 18 base pair address, a sequence long enough to specify a unique site in the human genome is used. A 6-zinc finger domain equivalent transcription factor functions as a highly specific and potent transcriptional regulator.

Peripheral Blood Mononuclear Cells (PBMCs): The mononuclear cell population used in the invention is obtained from patients in which the drug is intended to be used. PBMCs are isolated with the Ficoll-Hypaque gradient method, and the population thus obtained from a healthy donor consists of a mixture of about 5% B lymphocytes, 5–15% monocytes, 60–70% lymphocytes, and 5–15% natural killer cells (43, 44) The obtained cell population consists of the subsets B-lymphocytes, monocytes, T-lymphocytes, natural killer cells and a number of peripheral stem cells. One subset or a mixture of subsets of PBMCs are be used in this invention.

Reference set: A set of cellular responses correlated with in vivo responses.

In vivo response: Clinical result in a patient due to exposure to a chemical entity. For example, an in vivo response to a chemical entity in asthma could be changes in forced expiratory volume in one second (FEV1), as measured through a patient's use of a spirometer (26), or in depression as measured with HAM-D scores.

Cellular responses: Measurable in vitro responses in a cell type to the exposure of a chemical entity to the cell. These responses can include gene expression, increased motility, chemotaxis, contraction, relaxation, biosynthesis, secretion of signaling molecules, depolarization, repolarization, degranulation, adhesion, aggregation, change in metabolic rate, and immediate cellular responses.

Cellular response profiles: A set of cellular responses predictive for in vivo responses.

Chemical entity: Any substance tested to evaluate an in vivo response using a reference set of cellular responses. Examples of these are registered chemical entities, novel chemical entities, environmental reagents, and biologicals.

Efficacy: As defined in clinical studies (37, 38).

Adverse events: As defined in clinical studies (37,38)

Safety: As defined in clinical studies (37,38,39)

Patient: Individual with a clinical condition whose clinical outcome following exposure to chemical entities is being predicted.

Subject: Individual who is screened to acquire in vivo response versus cellular response correlations for reference sets.

This application describes a method of providing improved predictability for the efficacy and/or adverse event profile of chemical entities or effectors (novel chemical entities, registered chemical entities, environmental reagents, or biologicals) especially in the context of treating disease. The invention is a method that comprises finding correlations between in vitro cellular and in vivo responses to chemical entities, to create a new or utilize an already existing reference set of in vitro cellular responses to predict the effect the in vivo effect the chemical entity will have on a certain patient. The reference set is a cellular response profile obtained from a separate subject population with a disease phenotype comparable to the target patients. The in vitro cellular responses in PBMCs transformed into a bioassay using a specific ZFP are correlated with traditional in vivo clinical responses in terms of efficacy and adverse event profile. The reference in vitro data is then used to ascertain the relative efficacy and/or adverse event profile of novel chemical and biological entities to treat a disease in a similar group of patients.

Reference sets can be pre-existing or produced using the invention. The reference set is obtained by correlating the in vitro cellular response data gathered from a patient to an in vivo response data. The reference set contains clinical outcomes to a certain medical condition, each outcome accompanied by cellular response data gathered for the same subject. As described above, cellular responses can be one of many measurable responses a cell could have to the presence of a chemical entity.

Generally, these in vitro responses are detected by extracting blood from a subject or patient, and separating the peripheral blood mononuclear cells (PBMCs) from other parts of the blood (43, 44). These PBMCs are described above as a group of nucleated cells that are in the blood. Potentially, any type of cell could be used that could express a target of a chemical entity and produce a discernible cellular response that could be correlated with an in vivo response. Cell types that already express a target for the chemical entity being studied can simply be exposed to the chemical entity and their cellular response can be measured. PBMCs have targets for some chemical entities, but not for all chemical entities. In situations where the chemical entity being studied does not, or insufficiently has a target expressed in the cell type being exposed to it, the cells can be transduced using various techniques with a transcription factor such as a zinc finger protein (ZFP) that causes these targets to be expressed in the cells, as defined above. Other transcription factors could also be transduced into the cells as long as they somehow caused a target of the given chemical entity to be expressed in the cell.

Nucleic acids could also be introduced into the cells that encode transcription factors, or other proteins that could effect the expression of target molecules. The protein would not have to directly interact with the gene that it was modulating, it need only upregulate the expression of a target for a chemical entity.

After the cell is transduced and exposed to the chemical entity, some cellular response is measured. This measurement is then compared to reference measurements in a subject population from which a relevant subject set has been made. What makes up a relevant subject set depends on the condition being studied, but generally, it is a set of subjects that have the same or a similar clinical condition as the patient. If the patient had asthma, for example, subject sets from subjects with asthma being treated by different chemical entities with different clinical outcomes could be relevant.

The relevant reference set depends upon the disease or condition, and upon the markers for efficacy or adverse effects being measured. In this manner, certain cellular responses are correlated with certain in vivo responses. This gives some basis for prediction of a patient response to a drug when the patient displays a certain clinical condition. The methods of the present invention can also be used to study how certain novel drugs might affect a patient with a certain condition. The methods can also be used to choose which drug would be the most effective in treating a patient. The methods can also be used to study how certain chemical entities might interact with each other in the context of a patient's in vivo response. The methods of the present invention can also be used to ascertain certain adverse event or safety concern a chemical entity might induce when people are exposed to it. Finally, the methods can also be used to screen patients to ascertain which of them would respond to certain chemical entities under certain conditions, and which would not respond. Any clinical indication, in any therapeutic area could be studied with this method.

The in vitro/in vivo correlation can be obtained from a prospective study, in which both the in vitro and in vivo data has yet to be collected. The correlation can also be obtained from a retrospective study, in which in vivo data is already available, but in vitro data yet needs to be created. An example of the latter is when exposure to a chemical entity has caused life-threatening adverse events (such as valvular fibrosis in subjects who were treated with Fenfluramine) and, therefore, it would be unethical to administer this chemical entity to other subjects. In this case, subjects with, and subjects without the adverse events (in vivo data) after exposure to the chemical entity would be recruited, and in vitro data would be measured from the PBMCs of these subjects, in order to identify a cellular response profile to predict the adverse event in vivo response. This profile can be used to test new chemical entities or biologicals for their potential to cause these unacceptable adverse events.

In one embodiment of the invention, PBMCs are extracted from a patient with a certain disease (43, 44). The cells are transformed with a ZFP via retroviral infection. This ZFP is responsible for the expression of a target for a chemical entity that is to be screened for efficacy and/or adverse events in treating the disease. The PBMCs are then exposed to the chemical entity. RNA extraction is then performed as known in the art (41). This RNA is converted into a DNA library (34), and this is subtracted from another DNA library (35) made in a similar manner with untreated PBMCs, resulting in a number of genes being measured up or down regulated by the chemical entity. These up and down regulated genes are then compared to cellular response profiles associated with a positive outcome for the disease and/or with fewest adverse events. If the chemical entity's response in this patient's PBMCs correlates with a positive response in the reference set of cellular response profiles for this disease, then the drug is more likely to cause a positive outcome in the patient.

In another embodiment of the invention, the PBMCs from the above patient are split into a number of portions. Each portion is transduced with a different ZFP for a different chemical entity as above, and gene expression changes are detected for each portion as described above. The changes in gene expression of each of the chemical entities could be compared with a distinct cellular response profile in the cellular response profile, which profile is predictive for in vivo responses. The chemical entity that displays the most desirable profile could be used to treat the patient.

In another embodiment of the invention, the chemical entities in the above invention are novel chemical entities that had not been used before in the context of that disease state. They are screened for their ability to produce a cellular response that correlates with a positive clinical outcome.

In another embodiment, the chemical entities are known chemical entities that are used in a different disease state, but had not been used in the disease state that the patient above is displaying. They are screened for their ability to produce a cellular response that correlates with a positive clinical outcome.

In yet another embodiment of the invention, PBMCs are extracted from subjects with a certain disease being treated with a certain chemical entity. Differential gene expression is measured as described above. This is repeated for many subjects, collecting what genes are induced and repressed using a certain chemical entity in a certain disease state, and what the in vivo response to the treatment was in the subject. This data is collected using different chemical entities with the same disease to create a reference set of chemical response profiles correlated with in vivo responses. This reference set can be used, used, as described above, to create a cellular response profile predictive for in vivo results in patients with a certain disease.

In another embodiment, PBMCs are extracted from subjects that have been exposed to a chemical entity in their environment. The cellular responses of their PBMCs could then be compared with the cellular responses obtained from subjects in whom exposure resulted or did not result in some clinical condition, to identify a cellular response profile predictive for in vivo response.

In yet another embodiment, genes that are up or down regulated in the case of a desired in vivo response, could be attached to a microarray on a chip (42) or microbeads. In this manner, subtracted cDNA from a patient could be quickly tested to see if it correlates with a certain in vivo response.

EXAMPLES

Example 1

Use of the Invention to Mimic Phase III Clinical Trials

This invention carries key characteristics of a traditional phase III trial (38); except that drug testing is performed on cells of patients, instead of the patients themselves and the use of cellular responses, which are validated against in vivo responses, to predict in vivo traditional responses. The key characteristics of a traditional clinical trial which are addressed in the invention include:

Recruitment of patients with the desired disease phenotype.

The use of inclusion/exclusion criteria to select patients.

The use of efficacy endpoints which are validated and predictive for efficacy in the target population.

The use of safety (adverse event) endpoints which are validated and predictive for safety in the target patient population.

The calculation of a sample size sufficient to allow for the required statistical power.

The definition of success or failure of the test medicine on the basis of the choice of, and magnitude of desired change in endpoints validated against and predictive for success or failure in the target patient population.

Ethical review requirements such as study review and approval through an IRB.

Informed consent of the patients participating in the studies.

The same invention can also be used to predict which registered medication in a certain disease indication is likely to be effective and/or will have an acceptable adverse event profile in a given patient diagnosed with that disease (the concept of personalized medicine).

The same invention can also be used to predict, prior to participation, in phase II and phase III trials (38), which patients are likely to classify as a non-responder or responder to a NCE or biological intended to be tested in those clinical trials. Exclusion of non-responders allows for a smaller sample size needed in the study to ensure acceptable statistical power.

The same invention can also be used to identify alternative clinical indications for existing drugs, registered for use in a certain clinical indication.

The same invention can also be used to identify alternative clinical indications for novel NCEs or biologicals that failed in terms of efficacy during clinical trial testing in a certain indication.

Example 2

Use of Gene Expression Profiles as an In Vivo Response

The principle of pharmacotherapy is that a pharmacological response is initiated by a drug at its site of action on its so-called target. Several thousands of molecular targets have been cloned and are available as potential drug targets. These targets include more than 750 GTP-binding protein coupled receptors (GPCRs), over 100 ligand-gated ion channels, more than 60 nuclear receptors and 50 cytokines, and approximately 20 reuptake/transport proteins and a number of enzymes (15,16).

Signal transduction pathways involve a series or cascade of events that occur after a drug binds to its receptor, and culminate in the activation of effector mechanisms that result in a cellular response. Following binding of a drug to its receptor, immediate or late effects may occur. Immediate effects are due to modulation of cellular effector molecules that are already expressed by the target cell, and examples are increased motility, chemotaxis, contraction or relaxation, biosynthesis and secretion of other signaling molecules, depolarization or repolarization, degranulation, adhesion and aggregation, or a change in metabolic rate. Late effects are due to activation of nuclear transcription factors that either stimulate or inhibit gene expression. The cell response occurs later, following gene transcription (mRNA production), translation, protein synthesis and expression of newly synthesized proteins.

Gene expression profiles are a powerful tool to help dissect the mechanism of action of drugs and drug candidates. They will also increasingly contribute to the analysis of metabolic pathways for drugs, the understanding and prediction of adverse events in vitro and in vivo, as well a tool to predict the right dose and efficacy of a drug in the clinical setting.

Subsets of gene expression profiles can be used as a unique fingerprint of a specific drug action, and presumably, in cases in which the patients' disease condition improved, also as a fingerprint for clinical response. This principle was demonstrated in studying gene expression changes induced by toxic agents (toxicogenomics). Gene expression profiles are either causally linked to the toxic outcome or are downstream sequelae of the toxic exposure. Monitoring gene expression profiles, induced directly or indirectly by different classes of toxicants should eventually allow recognition of signature patterns that are representative of specific toxicities.

Once recognized, these patterns could be used to evaluate new compounds (pharmaceutical candidates) possessing undefined toxicities (17,18,19,20,21).

The same principle is used as demonstrated to study toxicology on a molecular biology basis, to study efficacy and adverse events related gene expression profiles. Treatment with drugs with known mechanisms of action can be used to define a reference of response to which new drugs can be compared (17).

Genes can be upregulated or downregulated as a result of the drug action on the cell. Typically hundreds of genes are involved, and publications report a range of 100–1000 genes (17,18), however the number of the same genes over/under-expressed in a repeated manner is only a small fraction of that number. Certain gene induction events occur consistently, while others are highly variable. A study showed that in HepG2 cells exposed to cis-platinum, 200 or more genes were differentially expressed, but only 14 genes were consistently differentially expressed (17).

The approach of using ZFPs to upregulate genes in order to express drug targets in PBMCs offers a unique opportunity to study downstream metabolic pathways in clinical responders and to differentiate these from clinical non-responders. This in turn may increase understanding of the underlying diseases, as it increases understanding of pharmacological drug actions at a molecular level.

Subsets of gene expression profiles can be used as a unique fingerprint of a specific drug action, and, in cases in which the patient's disease condition improved, also as a fingerprint for clinical response.

Example 3

Predicting Drug Efficacy and Adverse Events Against a Disease

In one embodiment of the invention a reference set of in vitro gene expression profiles predictive for in vivo pharmaco-responses (in terms of efficacy and adverse event profiles) are identified using a known drug (either drug A, B or C etc) registered for use in a certain clinical indication, for example disease X, to treat patients diagnosed with disease X. PBMCs are obtained from patients who are diagnosed with disease X, and these cells are used to create a bioassay, by expressing the drug target using specific ZFP in these cells. Drug responses induced by exposing drugs to the PBMC-based bioassay are obtained in parallel with clinical in vivo drug responses in these patients. Both cellular responses and in vivo patient responses are used to create a reference set. In this embodiment, the cellular in vitro responses are compared with the subject in vivo responses, both obtained within the same subject (within-subject comparison). A number of subjects diagnosed with disease X are treated with drug A, B or C, etc. If a given subject is treated with drug A, than the drug target for treatment A is expressed in the PBMCs of that subject, using a ZFP to express the target for drug A. This results in a PBMC-based bioassay, which is exposed to drug A to induce cellular in vitro responses. This procedure is also performed with subjects treated with other drugs B and C on PBMCs that were treated with ZFPs specific for drugs B and C.

Amongst the subjects treated with drug A, a number of subjects are selected who classify as in vivo responders as defined by standard traditional definitions for clinical response. A number of subjects are also selected who classify as non-responders according to the same definition. Cellular gene expression profiles obtained from the clinical responders are grouped, as are the cellular gene expression profiles of clinical non-responders. In the group of the clinical in vivo responders to drug A, profiles of in vitro gene expression that all or the majority individual responders have in common are identified, along with which profiles are not or hardly present in the non-responders to drug A. This common in vitro cellular response gene expression profile therefore has a high predictive value for in vivo subject response to drug A (predictive expression profile A). Similarly, profiles can be constructed for subjects treated with drug B or C.

The gene expression profiles predictive for response to drugs A, B or C are used for the creation of drug screening assays to test novel drugs with a pharmacological action similar to drug A, B, or C respectively. The gene expression predictive profiles predictive for response to drugs A, B or C are also used to develop the reference for the personalized medicine diagnostic product.

In addition, a gene expression profile that all or majority in vivo responders to drug A, B, C, etc have in common is identified, along with which profile is not or hardly present in the in vivo non-responders to drugs A, B, C, etc. This gene expression profile reflects gene expression patterns, which are associated with in vivo clinical responses ('getting better') irrespective of the mechanism of action of the drug used, as all three drugs, with a each a different mechanism of action to induce them. Therefore, this gene expression profile can be used to screen NCEs and biologicals with novel mechanisms to treat disease X.

In addition to identifying gene expression profiles predictive for efficacy of drugs A, B, C, etc in patients, gene expression profiles can also be identified, predictive for adverse events of these drugs in these patients. Patients experiencing a certain adverse event are separated from the patients who do not experience that adverse event. The gene expression profiles in the PBMCs of these patients (after transformation into a bioassay and exposed to the appropriate drug, as described for efficacy testing above) are analyzed to identify a gene expression profile that predominantly occurs in patients experienced with that adverse event, and not, or hardly, in patients who do not experience that adverse event. Differentially expressed genes are used to create customized microarrays or a different suitable assay, like microbeads, to allow a higher level of throughput testing.

Example 4

Screening NCEs for Efficacy and/or Adverse Event Profile

In another embodiment of the invention, the method is used to screen new chemical entities (NCEs) or biologicals for their efficacy and/or adverse event profile. By using a cellular response profile of validated gene expression profiles predictive for in vivo responses (translated into customized microarrays) by disease state, in vitro predictions about the in vivo efficacy of a novel NCE Y intended to treat disease X can be made, using the invention comprising the following components:
1. PBMCs from patients with disease X in which a future phase III study conduct is intended.
2. ZFP specifically expressing the target for NCE Y.
3. PBMC-based bioassay to be exposed to NCE Y.
4. mRNA extraction from these PBMCs.
5. Hybridization of mRNA to customized microarrays composed from gene expression profiles differentially expressed in clinical in vivo responders (in terms of efficacy and/or adverse event profile) compared to non-responders as described in example 3.
6. Analysis of hybridization pattern determines success of failure of the NCE Y in terms of efficacy and/or adverse event profile.

If NCE Y has a pharmacological mechanism of action similar to one of the registered drugs (for example drug A) used in the cellular response profile study, then the customized microarrays used in step 5 are composed from the differentially expressed gene data predictive for in vivo response (efficacy and/or adverse events) to drug A.

If NCE Y has a novel pharmacological mechanism of action intended for the treatment of disease X, then the customized microarrays used in step 5 are composed from the differentially expressed gene data predictive for in vivo response (efficacy and/or adverse events) that two or more registered drugs (each with a different pharmacological mechanism of action) have in common as described in Example 3. These commonly occurring gene expression data are assumed to predict disease modification, and are independent of the pharmacological mechanism of action of the individual drugs used. This is applicable for NCEs and biologicals.

Example 5

Screening Drugs for Relative Efficacy

In another embodiment of the invention, the method is used prior to drug administration, to ascertain which out of several candidate medications registered for a certain disease indication (X) is likely to be effective and/or has an acceptable adverse event profile in a given patient diagnosed with that disease X (the concept of personalized medicine). Gene expression profiles that specifically predict in vivo response to an individual drug A or B or C etc, indicated and marketed to treat a certain disease X are used to create a customized microarray, or other suitable technology like microbeads.

This in vitro diagnostic tool rapidly assesses whether a given patient diagnosed with disease X should be prescribed drug A, or B, or C etc. to improve the condition of disease X. PBMCs, of these patients are obtained, transformed into a bioassay, and exposed to drugs A, B, or C, etc., respectively, and the drug-induced cellular response (gene expression profile) is compared with a reference set of cellular responses correlated with in vivo responses. This cellular responses are obtained from a different but comparable set of subjects with disease X (as described in example 3), through in vitro/in vivo correlation. The cellular response in vitro gene expression profile predictive for in vivo response to drug A, B or C is used to create a microarray, or different suitable assay, for drug A, B or C, respectively (see below). This diagnostic test is comprised of the following components:

Obtain PBMCs from the patient with disease X, and divide into three fractions (if three drugs are intended to be tested).

Transfect one group of PBMCs with a ZFP specifically expressing target for drug A.

Expose drug A to this PBMC-based assay.

Extract mRNA from these PBMCs.

Hybridize mRNA to predictive gene expression array for drug A.

Analysis of hybridization pattern determines likely response or non-response to drug A in the new patient.

Transfect one group of PBMCs with a ZFP specifically expressing target for drug B.

Expose drug B to this PBMC-based assay.

Extract mRNA from these PBMCs.

Hybridize mRNA to predictive gene expression array for drug B.

Analysis of hybridization pattern determines likely response or non-response to drug B in the new patient.

Transfect one group of PBMCs with a ZFP specifically expressing target for drug C.

Expose drug C to this PBMC-based assay.

Extract mRNA from these PBMCs.

Hybridize mRNA to predictive gene expression array for drug C.

Analysis of hybridization pattern determines likely response or non-response to drug C in the new patient.

The in vitro response predictions of new patients to drugs A, B or C, etc allow selection of the drug treatment that is most likely to result in the best clinical outcomes in terms of efficacy and/or adverse event profile in these patients.

Example 6

Screening Patients for being Responders or Non-Responders to NCEs

In yet another embodiment, the method of the invention could be used to ascertain which patients diagnosed with disease X are likely to classify as a non-responder or responder to a NCE or biological intended to be tested in phase II and phase III clinical trials.

By using a cellular response profile of validated gene expression profiles predictive for in vivo responses translated into customized microarrays by disease state as described above, it is rapidly predictable in vitro whether a novel NCE (Z) intended to treat disease X will be effective in vivo in a clinical trial, using the invention comprising of the following components:

Isolate PBMCs from each of the patients with disease X, recruited to participate in the clinical trial ZFP specifically expressing the target for NCE-Z.

PBMC-based bioassay to be exposed to NCE-Z.

mRNA extraction from these PBMCs.

Hybridization of mRNA to customized microarrays. The microarray used depends on the pharmacological mechanism of action of NCE-Z (see below).

Analysis of hybridization pattern from patient to patient predicts which patient is likely to become a responder or a non-responder to NCE-Z.

If NCE Z has a pharmacological mechanism of action similar to one of the registered drugs (for example drug A) found in the cellular response profile, then the customized microarrays used in step 5 can be composed on the basis of differentially expressed gene data predictive for in vivo response (efficacy and/or adverse events) to drug A.

If NCE Z has a novel pharmacological mechanism of action, intended for the treatment of disease X, than the customized microarrays used in step 5 can be composed on the basis of the differentially expressed gene data predictive for in vivo response (efficacy and/or adverse events) that two or more registered drugs (each with a different pharmacological mechanism of action) have in common as described in example 3. These commonly occurring gene expression data are assumed to predict disease modification and are independent of the pharmacological mechanism of action of the individual drugs used. This is applicable for NCEs and biologicals.

Example 7

Finding New Uses for a Drug

In yet another embodiment of the invention, the method is used to ascertain new uses for already existing chemical entities.

This test tool identifies an alternative clinical indication for already marketed drugs that proved to be effective in a different clinical indication. This test tool allows to assessment of whether a drug (drug H) that is effectively used to treat disease X, is also effective in the treatment of disease Y in patients as follows:

Isolate PBMCs from patients diagnosed with disease Y.

Transfect the PBMC with a ZFP specifically expressing the target for drug H.

PBMC-based bioassay to be exposed to drug H.

mRNA extraction from these PBMCs.

Hybridization of mRNA to customized microarrays composed on the basis of cellular response gene expression profiles differentially expressed in clinical in vivo responders, and induced commonly by at least two different drug with different mechanisms of action in disease Y.

Analysis of hybridization pattern predicts whether drug H is likely to be effective in disease Y.

In the cellular response in vivo, responses are obtained in patients diagnosed with disease Y and treated with already marketed drugs, in parallel with in vitro gene expression analysis in PBMC-based assays from the same patients, exposed to the same drugs, to allow in vivo/in vitro comparison of endpoints.

In vivo response data from patients who respond to a given drug are correlated with the unique gene expression fingerprint derived from their PBMC-based assay. These gene expression studies in parallel with in vivo response monitoring are conducted with at least two drugs from a different pharmacological class, but effective in the same indication Y. Analysis across all responders in all drug categories identifies the subset of expressed genes that these two or more drugs have in common, and thus correlates with disease state improvement, regardless of the drug used. These predictive profiles are used to create customized microarrays, or other suitable technology. In vivo response can be obtained for drug efficacy and adverse event profile. This is applicable for chemical entities and biologicals.

Example 8

Screening NCEs that were not Effective Against One Disease to Ascertain Their Efficacy Against Another Disease In yet another embodiment of the invention, the method is used to identify new disease indications for an NCE (HF) that fail to be effective in an initially targeted disease. This test tool allows assessment of whether an NCE (drug HF) that was tested but failed to be effective in a certain disease X, would be effective in treating disease Y as follows:
  Isolate PBMCs from patients diagnosed with disease Y.
  Transfect PBMCs with a ZFP specifically expressing the target for NCE HF.
  PBMC-based bioassay to be exposed to NCE HF.
  mRNA extraction from these PBMCs.
  Hybridization of mRNA to customized microarrays composed from cellular response gene expression profiles differentially expressed in clinical in vivo responders, and induced commonly by at least two different drug with different mechanisms of action and registered in the treatment of in disease Y.
  Analysis of hybridization pattern predicts whether NCE HF is likely to be effective in disease Y.

In the reference study, in vivo responses are obtained in patients diagnosed with disease Y expression analysis in PBMC-based assays from the same patients, exposed to the same drugs, to allow in vivo/in vitro comparison of endpoints.

In vivo response data from patients who respond to a given drug are correlated with the unique gene expression fingerprint derived from their PBMC-based assay. These gene expression studies in parallel with in vivo response monitoring are conducted with at least two drugs from a different pharmacological class, but effective in the same indication Y. Analysis across all responders in all drug categories identifies the subset of expressed genes that these two or more drugs have in common, and thus correlates with disease state improvement, regardless of the drug used. These predictive profiles are used to create customized microarrays, or other suitable technology. In vivo responses are obtained for drug efficacy and adverse event profile. This is applicable for new chemical entities and biologicals.

Example 9

ZFP Transduction of PBMCs

PBMCs are isolated from a patient using the Ficoll-Hypaque gradient method (43,44). T-lymphocytes are a cell type in the subset of PBMCs used in ZFP transduction. T-lymphocytes are isolated from a patient's PBMC mixture using FACS sorting (27, 28), or by sorting with magnetic beads (29). T-lymphocytes can then be transduced with a ZFP through a retroviral technique (30), following pre-activation steps (with anti-CD3, IL-2 and/or phytohaemagglutinin (PHA), as used widely (31)) and co-localization of retroviral particles and target cells on a template.

When transduction efficiency is insufficient, it is necessary to enrich the cell mixture, by separating out the non-transduced cells. To distinguish between transduced and non-transduced cells, the presence of a marker gene on the retrovirus may be used (30). This marker gene can encode either an antibiotic resistance protein (30), or for an easily detectable marker protein such as GFP (30). Enrichment in regard to successfully transduced cells can be obtained by exposing cells to an appropriate antibiotic or, if a GFP was used, by fluorescence-activated cell sorting.

If it is impossible to use a marker gene, the efficiency of transduction can be determined by analyzing expression of the transgene (i.e., zinc finger protein) or target gene (up-regulated by zinc finger protein) using flow cytometry. In case the target gene product following transcription and translation is a cell surface protein, a primary antibody specific for this protein can be used, combined with a fluorescent-labeled secondary antibody, followed by FACS sorting. If the target gene product is an intracellular protein, a cell-permeabilizing step is needed prior to the FACS sorting (32) following addition of the primary and secondary fluorescent-labeled antibody.

In addition to T-lymphocytes, B-lymphocytes can be used to create cell lines (for example using Epstein-Barr Virus infection to stimulate the B-cells (40)) expressing the drug target of interest. Also subsequently, peripheral blood stem cells can be used with or without mobilization steps, which can be stimulated to proliferate through specific cytokines (21,22). Because these stem cells are not terminally differentiated, they may offer a better alternative than T-lymphocytes to ensure that the expressed drug targets are functionally integrated in these cells.

Among the various viral vectors, retroviral vectors are preferred because they are easy to use, fast to prepare and induce long term expression of the target following integration in the host genome (30). However, retroviruses only infect dividing cells. If this is a significant disadvantage, alternatives such as lentiviral vectors (33), which can infect resting cells, are used.

In a more specific example, a ZFP for Albuterol, a $\beta 2$-adrenergic receptor agonists used as a cAMP mediated bronchodilator in Asthma (23), is constructed and tested using the above methods. The technical feasibility of the use of the Albuterol ZFP is considered successful, if:
  1. This ZFP is capable of upregulating expression of the $\beta 2$-adrenergic receptor in the T-lymphocytes.
  2. The expressed $\beta 2$-adrenergic receptor is successfully integrated in the T-lymphocytes.

The proof of technical feasibility experiment includes the following steps:
  Selection of a ZFP protein for this drug target.
  Configuration of the ZFP using proprietary linkers.
  Confirmation of the specificity of the ZFP.
  Attachment of a regulatory domain to configure ZFP.
  The transfer of ZFP to retrovirus for cell delivery.
  Test ZFP for ability to up-regulate target receptor in PBMCs, using specific antibodies.
  Exposing the successfully modified T-lymphocytes with Albuterol, and measuring intracellular cAMP production.

Increased intracellular levels of cAMP following expose of these T-lymphocytes with Albuterol, as compared to T-lymphocytes, not transduced with the ZFP, and exposed to Albuterol, is regarded as proof of technical feasibility for this ZFP.

Example 10

Analysis of Differentially Expressed Genes cDNA library construction (34) and subtraction (35) can be used to identify differentially expressed genes in clinical responders and non-responders. In addition, available microarrays can also be used for this purpose (36). Response and non-response can be obtained in vivo from the target patient population, in which the NCE/drug is intended to be used, and is defined according to standard clinical definitions (37, 38, 39).

PBMCs in which the drug target is expressed by means of ZFP transduction are selected by flow cytometry or magnetic beads, as detailed above. PBMCs in which the target for a drug is expressed are incubated with that drug. Incubation is with two separate doses (intermediate and high), for three time durations (0 (predose), 8 hour, and 24 hour).

To enable the cDNA library construction and subtraction, mRNA is extracted (41) from a minimum of 10 million successfully transduced cells that are treated with drug as described above. The following libraries were pooled:
  I. Postdose responders: cDNA from cells from a selected number of responders (R) are pooled, including the two doses for both postdose time points.
  II. Postdose non-responders: cDNA from cells from a selected number of non-responders (NR) are pooled, including the two doses for both postdose time points.
  III. Predose responders: cDNA from cells from responders (R), as selected under I, are pooled from the predose samples.
  IV. Predose non-responders: cDNA from cells from non-responders (NR) as selected under II, are pooled from the predose samples.

The following subtracted libraries are considered from pooled material:
  I. Postdose (R)-Postdose (NR)
  II. Postdose (NR)-Postdose (R)
  III. Predose (R)-Predose (NR)
  IV. Predose (NR)-Predose (R)
  V. Postdose (R)-Predose (R)
  VI. Predose (R)-Postdose (R)
  VII. Postdose (NR)-Predose (NR)
  VIII. Predose (NR) Postdose (NR)

This is followed by 3'sequencing of clones obtained from the subtractions. Each 3'-terminal sequence is searched on-line using the BLAST program at the NCBI site for possible matches in the non-redundant and EST public databases. Accession numbers from the BLAST search are used to search the UNIgene database to identify non-redundant Unigene clusters. A Unigene search is also be performed on the public EST sequence libraries for selected Stratagene libraries. If the 3'-terminal sequence does not allow the identification, this clone undergoes 5'-terminal sequencing.

Hybridization patterns of probes prepared from the subtracted libraries I–VI are used to create our own customized microarrays displaying subtracted sequences. This is followed by hybridization of probes of all individual patient samples onto the microarrays displaying the subtracted libraries. This step is needed to demonstrate that differentially expressed genes as obtained from subtractions of pooled samples, are differentially expressed in all or the majority of the individual responders.

Commercially available microarrays can also be used to examine differentially expressed genes, using a hybridization reaction between the sequences on the microarray and a fluorescent sample (36). After hybridization, the microarrays are read with high-speed fluorescent detectors and the intensity of each spot is quantified. The location and intensity of each spot reveal the identity and amount of each sequence present in the sample. The data are then mined and modeled using the tools of computational biology. Thousands, or tens of thousands of gene fragments can be present on a single microarray.

This technique can be used on multiple drugs with the same batch of isolated PBMCs. The batch is split into as many groups as there are drugs to be tested, and the same procedure is run on each group with their own ZFPs and drugs.

Example 11

Ascertaining Drug Efficacy in Conjunction with Albuterol in Asthma

Screening of drug efficacy can be conducted in asthma (24,25). For many patients, the disease has its roots in infancy, and both genetic factors and environmental factors contribute to its inception and evolution. Of the chronic diseases of childhood, asthma is the most common, with reported prevalence in children ranging from 3% to 27% across different countries. In the U.S. alone, about 17 to 20 million individuals have asthma, and the total sales of respiratory therapies exceed $17 billion a year. There are five major classes of asthma drugs, including β2-adrenergic receptor agonists, leukotriene antagonists, inhaled corticosteroids, phophodiesterase inhibitors and anticholinergic drugs. The targets of these drugs are extensively studied and well defined, and there are currently 28 NCEs being developed for respiratory and lung diseases.

The primary objective is to identify a set of gene expression profiles in T-lymphocytes (with expressed β2-adrenergic receptor using specific ZFP) in asthma patients treated effectively with Albuterol. Albuterol is a β2-adrenergic receptor agonists used as a bronchodilator in asthma. β2-adrenergic receptor agonists relax bronchial smooth muscle through cyclic AMP (cAMP)-mediated pathways (23). An additional objective is to identify a set of gene expression profiles predictive for most frequently occurring adverse events following a single dose of Albuterol in our study.

Twenty to forty patients diagnosed with moderate to severe asthma, with defined clinical phenotype, are recruited and asked to interrupt corticosteroid treatment for 24 hours and treatment with β2-adrenergic receptor treatment for 12 hours prior to participation in this study. The patients are treated with the bronchodilator Albuterol, a β2-adrenergic receptor. They are monitored for in vivo efficacy for bronchodilation, using the forced expiratory volume in one second (FEV1), and adverse events. Simultaneously, in vitro gene expression data is obtained from T-lymphocytes from the same patients. FEV1 and adverse event are recorded prior and at regular intervals after Albuterol treatment.

The FEV1 is the primary measurement assessed with spirometry for evaluating asthma severity and assessing change in the degree of airway obstruction (26). Spirometry is an excellent procedure for documenting changes in Asthma, because it is reliable, reproducible, and standardized (26). The reported positive clinical response rate in terms of bronchodilation after Albuterol treatment varies from 26.3% (7) to 54% (23).

Adverse events are collected for at least 8 hours after administration of Albuterol. Prior to administering Albuterol to the patients, T-lymphocytes are isolated from these patients, and transformed into bioassays using specific ZFPs to express β2-adrenergic receptors, followed by drug exposure and mRNA analysis and sequencing.

Although β2-adrenergic receptors are expressed in T lymphocytes of healthy people, in drug-free asthmatic patients, β2-adrenergic receptor density (and hence cAMP response) is significantly reduced, without changes in affinity of these receptors to the ligand (45,46,47). Therefore T-lymphocytes of asthmatic patients would offer an ideal cell type to assess the potential of a specific ZFP to increase expression of β2-adrenergic receptors in these cells.

Gene expression data of clinical responders is separated from clinical non-responders and a gene expression profile is identified that occurs in all or the majority of responders, but absent or hardly present in non-responders. Similarly, a gene expression profile is identified that occurs in all or the majority of adverse responders, but absent or hardly present in non-adverse responders, Predictive cellular response gene expression profiles are used to design customized microarrays or microbeads. These microarrays or microbeads can either be used to develop screening tools or to predict whether a patient responds to a specific Albuterol (diagnostic).

The embodiments explained above are for explanatory purposes only. In no way should they limit the invention from other embodiments not listed here.

All references included above are incorporated in their entirety.

REFERENCES

1. Lehman Brothers Report. The Fruits of Genomics. January 2001.
2. Boston Consulting Group. The Revolution in R&D: The Impact of Genomics. June 2001.
3. Houlihan, Lokey, Howard&Zukin. Advanced Valuation Techniques in Life Sciences; February 2001.
4. Liggett S B. Pharmacogenetic applications of the human genome project. Nature Medicine 2001; 7:281–283.
5. Drysdale C M, McGraw D W, Stack C B, Stephens J C, Judson R S, Nandabalan K, Arnold K, Ruano G, Liggett S B. Complex promoter and coding region β2-adrenergic receptor haplotypes alter receptor expression and predict in vivo responsiveness. PNAS 2000; 97:10483–10488.
6. Drazen J F, Yandava C N, Dube L, Szcerback N, Hippensteel R, Pillari A, Israel E, Schork N, Silverman E S, Katz D A, Drajesk J. Pharmacogenetic association between ALOX5 promoter genotype and the response to anti-asthma treatment. Nature Genetics 1999; 22:168–170.
7. Martinez F D, Graves P E, Baldini M, Solomon S, Erickson R. Association between genetic polymorphisms of the β2-adrenoceptor and response to albuterol in children with and without a history of wheezing. J Clin Invest 1997; 100:3184–3188.
8. Poste G. The right treatment for the right patient. Scrip Magazine, January 2000: 11–14.
9. Kang J S, Kim J S. Zinc Finger Proteins as designer transcription factors. J Biol Chem 2000; 275:8742–8748.
10. Kim J S, Pabo C O. Getting a handhold on DNA: Design of poly-zinc finger proteins with femtomolar dissociation constants. PNAS 1998; 95:2812–2817
11. Beerli R R, Segal D J, Dreier B, Barbas C F III. Toward controlling gene expression at will: specific regulation of the erbB2/HER-3 promoter by using polydactyl zinc finger proteins constructed from modular building blocks. PNAS 1998; 95:14628–14633.
12. Beerli R R, Dreier B, Barbas C F III. Positive and negative regulation of endogenous genes by designed transcription factors. PNAS 2000; 97:1495–1500.
13. Pierce J H, Ruggierro M, Fleming T P, Di Fiore P R, Greenberger J S, Varticovski L, Schlessinger J, Rovera G, Aaronson S A. Signal transduction through the ECF receptor transfected in IL-3-dependent hematopoetic cells. Science 1988; 239:628–631.
14. Riese D J II, van Raaij T M, Plowman G D, Andrews G C, Stern D F. The cellular response to neurogulins is governed by complex interactions of the erbB receptor Family. Molecular and Cellular Biology 1995; 15:5770–5776.
15. Ohlstein E H, Ruffolo R R Jr, Elliott J D. Drug discovery in the next millennium. Annual Rev Pharmacol Toxicol 2000; 40:177–191
16. Drews J. Drug Discovery: A Historical Perspective. Science 2000; 287:1960–1964.
17. Burczynski M E, McMillian M, Ciervo J, Li L, Parker J B, Dunn R T II, Hicken S, Farr S, Johnson M D. Toxicogenomics-based discrimination of toxic mechanism in HepG2 human hepatoma cells. Toxicological sciences 2000; 58:399–415.
18. Afshari C A, Nuwaysir E F, Barret J C. Application of complementary DNA microarray technology to carcinogen identification, toxicology, and drug safety evaluation. Cancer Res 1999; 59; 4759–4760.
19. Braxton S, and Bedillion T. The integration of microarray information in the drug development process. Curr Opin Biotech 1998; 9:643–649
20. Nuwaysir E F, Bittner M, Trent J, Barrett J C, Afshari C A. Microarrays and toxicology: The advent of toxicogenomics. Mol Carcinog 1999; 24:153–159.
21. Aurran-Schleinitz T, Imbert A, Humeau L, Bardin F, Charbord P, Chabannon C. Early progenitor cells from human mobilized peripheral blood express low levels of the flts receptor, but exhibit various biological responses to flts3-L. Br J Haematol 1999; 106:357–367
22. Pollard Y, Watts M J, Grant D, Chvada N, Linch D C, Machin S J. Use of the haemopoietic progenitor cell count of the Sysmex SE-9500 to refine apheresis timing of peripheral blood stem cells. Br J Haematol 1999; 106: 538–544
23. Wilber S T, Wilson J E, Blanda M, Gerson L W, Meerbaum S H, Janas G. The broncholdilator effects of intravenous glucagon in asthma exacerbation: A randomized, controlled trial. Annals of Emergency Medicine 2000; 36:427–431
24. Busse W W, Lemanske R F Jr. Asthma. NEJM, 2001; 344:350–362.
25. Barnes P J. Inhaled glucocorticoids for asthma. NEJM 1995; 332:868–875.
26. Blaiss M S. Outcomes analysis in asthma. JAMA 1997; 278: 1874–1879.
27. Galboraith, D. W., et al., Flow cytometric analysis and FACS sorting of cells based on GFP accumulation. Methods in Cellular Biology 1999; 58:315–41.
28. Nielsen, M. B., et al., Status of activation of circulating vaccine-elicited CD8+T cells. Journal of Immunology Aug. 15, 2000; 165(4):2287–96.
29. Luxembourg, A. T. et al., Biomagnetic isolation of antigen-specific CD8+T cells usable in immunotherapy. Nature Biotechnology Mar, 1998; 16(3):281–5.
30. *Current Protocols in Molecular Biology* Ed. Ausubel, F. M., et al. 1998 Chapter 9.

31. Nanki, T., et al., Cutting edge: stromal cell-derived factor-1 is a costimulator for CD4+T cell activation. Journal of Immunology May 15, 2000; 164(10):5010–4.
32. Berki, T., et al. Production and flow cytometric application of a monoclonal anti-glucocorticoid receptor antibody. Journal of Immunology Methods May 1, 1998; 214(1–2):19–27.
33. Naldini, L. et al. Lentiviral vectors. Advances in Virus Research 2000; 55:599–609.
34. *Current Protocols in Molecular Biology* Ed. Ausubel, F. M., et al. 1998 Chapter 5.1–5.7
35. *Current Protocols in Molecular Biology* Ed. Ausubel, F. M., et al. 1998 Chapter 5.8–5.9
36. Winzeler, E. A., et al. Fluorescence-based expression monitoring using microarrays. Mthods in Enzymology 1999; 306:3–18.
37. *The Textbook of Pharmaceutical Medicine. $2^{nd}$ edition.* Eds. Griffin J P, O'Grady J, Wells FO. Executive Editor: D'Arcy P F. The Queen's University of Belfast, publishers.
38. *New Drug Development: A Regulatory Overview.* Revised $5^{th}$ edition. Ed. Mathieu M. Parexel, publishers
39. *Drug Safety. A Shared responsibility.* Glaxo Group Research. ISBN 0443046557. Churchill Livingstone, publishers.
40. Bejarano, M. T., et al. Interleukin-10 abrogates the inhibition of Epstein-Barr virus-induced B-cell transformation by memory T-cell responses. Blood Dec. 1, 1998; 92(11):4256–62.
41. *Current Protocols in Molecular Biology* Ed. Ausubel, F. M., et al. 1998 Chapter 4.
42. Hess, K. R. et al., Microarrays: handling the deluge of data and extracting reliable information. Trends Biotechnol. November 2001, 19(11):463–8.
43. Reichert T, et al. Lymphocyte subset reference ranges in adult Caucasians. Clin Immunol Immunopathol 1991; 60:190–208.
44. Boyum A. Separation of white blood cells. Nature 1964; 204:793–794.
45. Gillespie E, Valentine M D, Lichtenstein L M. Cyclic AMP metabolism in asthma: studies with leukocytes and lymphocytes. J Allergy Clin Immunol 1974; 53:27–33
46. Parker C W, Smith J W. Alternations in cyclic adenosine monophosphate metabolism in human bronchial asthma. Leukocyte responsiveness to beta-adrenergic agents. J Clin Invest 1973; 52:48–59.
47. Motojima S, Fukada T, Makino S. Measurement of β2-adrenergic receptors on lymphocytes in normal subject and asthmatics in relation to β2-adrenergic hyperglycaemic response and bronchial responsiveness. Allergy 1983; 38:331–337.
48. Jenne J W. Whither beta-adrenergic tachyphylaxis? J Allergy Clin Immunol 1982; 70:413–416.
49. Green S A, Turki J, Bejarano P, Hall I P, Liggett S B. Influence of β2-adrenergic receptor genotypes on signal transduction in human airway smooth muscle cells. Am J Respir Cell Mol Biol 1995; 13:25–33.

I claim:

1. A method of predicting a patient's in vivo response to a chemical entity, comprising: (i) creating a set of reference cellular responses, wherein the cellular responses are selected from the group consisting of gene expression, increased motility, chemotaxis, contraction, relaxation, biosynthesis, secretion of signaling molecules, depolarization, repolarization, degranulation, adhesion, aggregation, change in metabolic rate, and immediate cellular responses, to the chemical entity, wherein the chemical entity is selected from the group consisting of a registered chemical entity, a novel chemical entity, an environmental reagent, and a biological in peripheral blood mononuclear cells, wherein peripheral blood mononuclear cells are selected from the group consisting of T-lymphocytes, B-lymphocytes, monocytes, natural killer cells, and peripheral blood stem cells, which cellular responses are correlated with in vivo responses in a population of subjects; (ii) drawing said peripheral blood mononuclear cells from the patient; (iii) detecting the cellular response of the patient's peripheral blood mononuclear cells to the chemical entity, wherein step (iii) comprises: (a) transducing the patient's peripheral blood mononuclear cells with a zinc finger protein that specifically expresses or upregulates the target for the chemical entity; (b) exposing the transduced peripheral blood mononuclear cells to the chemical entity and (c) detecting resultant cellular responses of the patient's peripheral blood mononuclear cells' to the chemical entity; (iv) identifying the cellular response in the reference set of step (i) that corresponds to the patient's cellular response of step (iii); and (v) determining the in vivo response which correlates with the cellular response in the reference set identified in step (iv); wherein the patient is predicted to have the in vivo response determined in step (v) when exposed to the chemical entity in vivo.

2. The method of claim 1, wherein step (iii) further comprises after step (b) and before step(c)(I) performing mRNA extraction on the exposed peripheral blood mononuclear cells of step (b); (II) constructing a cDNA library from the extracted RNA and (III) performing a cDNA subtraction with another cDNA library.

3. The method of claim 1, wherein the patient's peripheral blood mononuclear cells are divided into two or more portions and each portion is tested on a different chemical entity.

4. A method for predicting an in vivo response that a chemical entity, wherein the chemical entity is selected from the group consisting of a registered chemical entity, a novel chemical entity, an environmental reagent, and a biological, will cause in a patient afflicted with a specific disease, comprising: (i) drawing peripheral blood mononuclear cells, wherein peripheral blood mononuclear cells are selected from the group consisting of T-lymphocyte, B-lymphocyte, monocytes, natural killer cells, and peripheral blood stem cells from the patient diagnosed with the specific disease; (ii) performing gene expression analysis on the peripheral blood mononuclear cells of the patients, wherein step (ii) comprises: (a) transducing the patient's peripheral blood mononuclear cells with a zinc finger protein that specifically expresses or upregulates the target for the chemical entity: (b) exposing the transduced peripheral blood mononuclear cells to the chemical entity: (c) performing mRNA extraction on the exposed peripheral blood mononuclear cells of step (ii): (d) constructing a cDNA library from the extracted RNA: (e) performing a cDNA subtraction with another cDNA library; and (f) detecting resultant cellular responses of the patient's peripheral blood mononuclear cells' to the chemical entity; (iii) comparing the results of the gene expression analysis of step (ii) to a reference set of gene expression analysis results that are correlated with an in vivo response to the specific disease; and (iv) determining the in vivo response which correlates with the cellular response, wherein the cellular response is selected from the group consisting of gene expression, increased motility, chemotaxis, contraction, relaxation, biosynthesis, secretion of signaling molecules, depolarization, repolarization, degranulation, adhesion, aggregation, change in metabolic rate, and immediate cellular responses in the reference set; wherein the chemical entity is predicted to cause the in vivo response determined in step (iv).

5. The method of claim 4, wherein the patient's cells are divided into two or more portions and each portion is tested on a different chemical entity.

6. A method for predicting whether a patient diagnosed with a specific disease is likely to respond positively, wherein the positive response is selected from the group consisting of efficacy, lack of adverse effect and safety to a chemical entity, wherein the chemical entity is selected from the group consisting of a registered chemical entity, a novel chemical entity, an environment reagent, and a biological, comprising: (i) creating a set of reference cellular responses, wherein the cellular response is selected from the group consisting of gene expression increased motility, chemotaxis, contraction, relaxation, biosynthesis, secretion of signaling molecules, depolarization, repolarization, degranulation, adhesion, aggregation, change in metabolic rate, and immediate cellular responses to the chemical entity in peripheral blood mononuclear cells, wherein peripheral blood mononuclear cells are members of the group consisting of T-lymphocytes, B-lymphocytes, monocytes, natural killer cells, and peripheral blood stem cells that are correlated with in vivo responses in a population of subjects afflicted with the specific disease that have responded positively to the chemical entity; (ii) capturing these reference cellular responses on a suitable assay; (iii) drawing peripheral blood mononuclear cells from the patient, wherein step (iii) comprises (a) transducing the patient's peripheral blood mononuclear cells with a zinc finger protein that specifically expresses or upregulates the target for the chemical entity; (b) exposing the transduced peripheral blood mononuclear cells to the chemical entity and (c) detecting resultant cellular responses of the patient's peripheral blood mononuclear cells' to the chemical entity; (iv) detecting the cellular response of the patient's peripheral blood mononuclear cells to the chemical entity; (v) identifying the cellular response in the reference set of step (i) that corresponds to the patient's in vivo response; and (vi) determining the in vivo response which correlates with the cellular response obtained in (iii), wherein the patient having a cellular response that correlates with the cellular response in the reference set is predicted to be likely to respond positively to the chemical entity.

7. The method of claim 6, wherein the patient's cells are divided into two or more portions and each portion is tested on a different chemical entity.

8. The method of claim 6, wherein step (iii) further comprises after step (a) and before step (c): (I) performing mRNA extraction on the exposed peripheral blood mononuclear cells of step (b); (II) constructing a cDNA library from the extracted RNA and (III) performing a cDNA subtraction with another cDNA library.

9. The method of claim 6, wherein the suitable assay is a microarray.

10. The method of claim 6, wherein the suitable assay is microbeads.

* * * * *